US010750942B2

(12) United States Patent
Aleckner

(10) Patent No.: US 10,750,942 B2
(45) Date of Patent: Aug. 25, 2020

(54) ADAPTIVE LARYNGOSCOPE AND ADAPTIVE BLADE FOR A LARYNGOSCOPE

(71) Applicant: Karl Storz SE & Co. KG, Tuttlingen (DE)

(72) Inventor: Martina Aleckner, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 0 days.

(21) Appl. No.: 15/656,101

(22) Filed: Jul. 21, 2017

(65) Prior Publication Data

US 2018/0020907 A1   Jan. 25, 2018

(30) Foreign Application Priority Data

Jul. 21, 2016 (DE) .................. 10 2016 113 498

(51) Int. Cl.
*A61B 1/267* (2006.01)
*A61B 1/005* (2006.01)

(52) U.S. Cl.
CPC ............ *A61B 1/267* (2013.01); *A61B 1/0055* (2013.01)

(58) Field of Classification Search
CPC . A61B 1/00064; A61B 1/0056; A61B 1/0055; A61B 1/00105
See application file for complete search history.

(56) References Cited

U.S. PATENT DOCUMENTS

| 5,584,795 A | 12/1996 | Valenti |
| 6,053,166 A | 4/2000 | Gomez |
| 8,821,388 B2 * | 9/2014 | Naito .................. A61B 1/0055 600/141 |
| 9,050,047 B2 * | 6/2015 | Chen ...................... A61B 1/267 |
| 2005/0273085 A1 * | 12/2005 | Hinman ............... A61B 1/0055 606/1 |
| 2007/0293865 A1 * | 12/2007 | Ko ....................... A61B 17/688 606/916 |

(Continued)

FOREIGN PATENT DOCUMENTS

| DE | 29921801 U1 | 3/2000 |
| DE | 60221889 T2 | 5/2008 |
| FR | 2821736 B1 | 9/2002 |

OTHER PUBLICATIONS

European Search Report Application No. 17182098.8 completed: Oct. 31, 2017; dated Nov. 13, 2017 7 Pages.

(Continued)

*Primary Examiner* — Ellen C Hammond
*Assistant Examiner* — Tara Rose E Carter
(74) *Attorney, Agent, or Firm* — McGlew and Tuttle, P.C.

(57) ABSTRACT

An adaptive blade for a laryngoscope includes a proximal end, a distal end, a first chain arranged between the ends and composed of a plurality of chain links connected in pairs in an articulated manner, a second chain arranged between the ends and composed of a plurality of chain links connected in pairs in an articulated manner, and a spacer component, connected at a first end in an articulated manner to the first chain, and connected at a second end in an articulated manner to the second chain. One or more or all of the articulated connections between the chain links of the first chain, the chain links of the second chain and the spacer component are provided as a form-fit hinge.

18 Claims, 5 Drawing Sheets

(56) References Cited

U.S. PATENT DOCUMENTS

| | | | |
|---|---|---|---|
| 2007/0293875 A1* | 12/2007 | Soetikno | A61B 17/1227 |
| | | | 606/142 |
| 2008/0051802 A1* | 2/2008 | Schostek | A61B 1/00135 |
| | | | 606/108 |
| 2010/0261968 A1* | 10/2010 | Nearman | A61B 1/00041 |
| | | | 600/188 |
| 2011/0196204 A1 | 8/2011 | Setty et al. | |
| 2012/0220830 A1* | 8/2012 | Yang | A61B 1/0053 |
| | | | 600/137 |
| 2013/0310650 A1 | 11/2013 | Hales et al. | |
| 2015/0031957 A1 | 1/2015 | Chen et al. | |

OTHER PUBLICATIONS

German Search Report Application No. 10 2016 113 498.8 Completed Date: Mar. 8, 2017; dated Mar. 13, 2017 10 pages.

* cited by examiner

Fig. 8
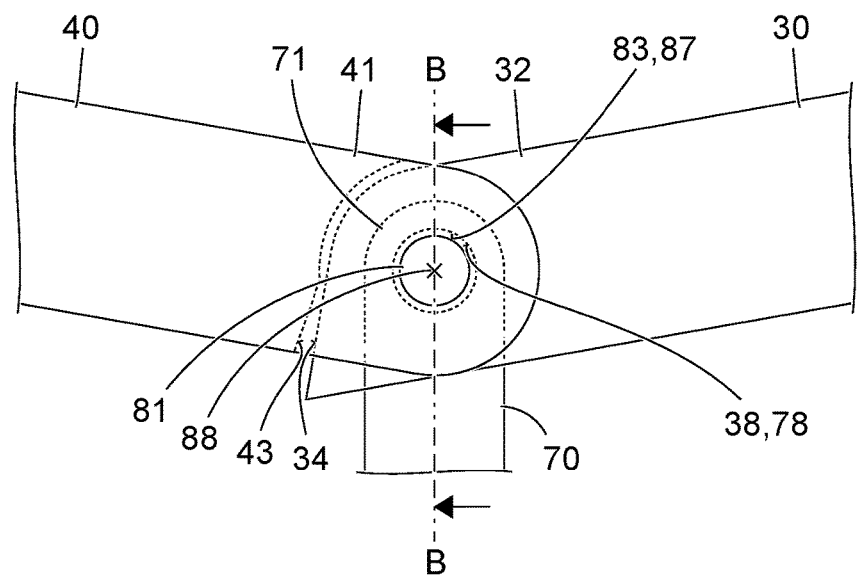
Fig. 9  B-B
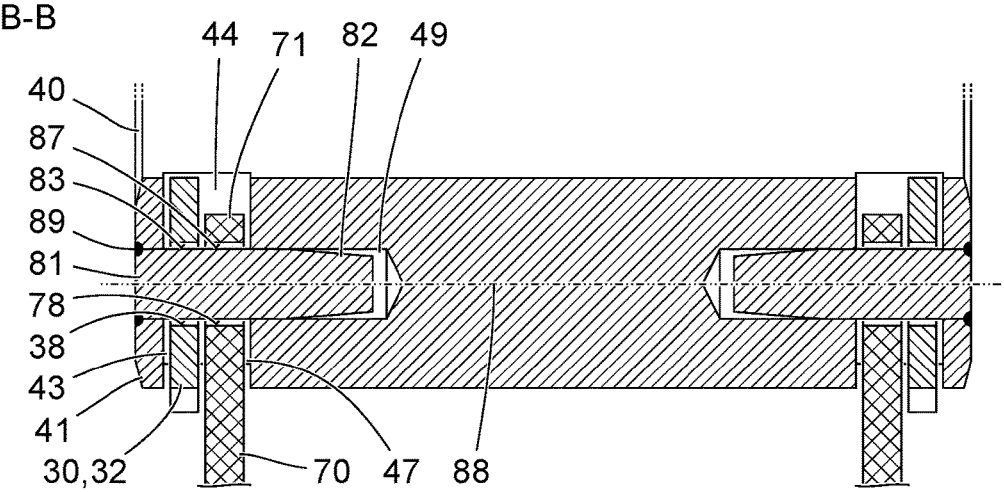

ADAPTIVE LARYNGOSCOPE AND ADAPTIVE BLADE FOR A LARYNGOSCOPE

TECHNICAL FIELD

The present invention relates to an adaptive laryngoscope, in particular an adaptive intubation laryngoscope, or an adaptive laryngoscope for laryngoscopy, surgery of the larynx or for other purposes in otorhinolaryngology. The present invention further relates to an adaptive blade for such a laryngoscope or for an intubation device.

BACKGROUND

To perform endotracheal intubation in anesthesia, emergency medicine and intensive care and to perform surgery of the larynx, an unobstructed access to the larynx, the vocal cords and, ultimately, often also the trachea is needed for the intubation or for surgical procedures. In these cases, a laryngoscope is used to push the tongue forward or in the rostral direction. A laryngoscope generally comprises a blade of greater or lesser curvature, at the proximal end of which blade a handle is arranged approximately at a right angle.

To facilitate adaptation to the anatomy of the patient, the blade is generally exchangeable. An intubation kit includes a large number of blades of different length and different curvature. Moreover, different designs of blade are available for different uses and/or to meet different preferences of the medical personnel, for example blades after Macintosh, Miller, Dörges and McCoy, the latter with a movable distal end.

A laryngoscope with a deformable distal end is also described in WO 97/30626 (later also published as U.S. Pat. No. 6,174,281 B1). The blade 4 of the laryngoscope has several slits 40 in a central portion 14. The slits 40 divide the central portion 14 into segments 42, which are connected to each other only by narrow webs that act as flexure bearings.

EP 1 040 999 A2 describes a component for taking up forces, in which struts 11, 11a connect opposite regions of an outer skin 12, 12a to each other.

EP 2 241 403 A1 describes a manipulator tool with two flexible cheeks 8, 10. At the distal end 6 of the manipulator tool 1, the cheeks 8, 10 are connected to each other directly and also by several hinge elements 20.

DE 10 2007 026 721 A1 describes a medical gripping tool for holding body parts. The medical gripping tool 1 comprises several branches 1, each with two opposite cheeks between which connecting elements extend.

DE 10 2005 010 380 B4 describes a gripping tool with self-adaptive kinematics.

It is an object of the present invention to make available an improved adaptive blade for a laryngoscope and to make available an improved adaptive laryngoscope.

SUMMARY

This object is achieved by the subject matter of the independent claims.

Developments are set forth in the dependent claims.

An adaptive blade for a laryngoscope comprises a proximal end, a distal end, a first chain arranged between the proximal end and the distal end of the adaptive blade and composed of a plurality of chain links which are each connected in pairs in an articulated manner, a second chain arranged between the proximal end and the distal end of the adaptive blade and composed of a plurality of chain links which are each connected in pairs in an articulated manner, and a spacer component, wherein a first end of the spacer component is connected in an articulated manner to one of the chain links of the first chain, wherein a second end of the spacer component is connected in an articulated manner to one of the chain links of the second chain, and wherein one or more or all of the articulated connections between the chain links of the first chain, the chain links of the second chain and the spacer component comprise a form-fit hinge.

The adaptive blade is provided and designed in particular to form a laryngoscope which is usable for intubation or for microsurgery of the larynx or for other purposes in otorhinolaryngology. The proximal end of the adaptive blade can be mechanically connected to a handle in a permanent manner, in particular for the full expected lifetime of the laryngoscope, so as not to be separable without destruction. In particular, a proximal end of the adaptive blade can be formed completely or partially in one piece with the handle, for example as a simultaneously produced molding made of plastic, metal or another sufficiently elastic material. Alternatively, a coupling mechanism (for example in the form of a bayonet connection, a screw connection or a latch connection) can be provided at the proximal end of the adaptive blade for the purpose of coupling the latter to a handle in such a way as to be releasable therefrom without destruction, either once or repeatedly.

The distal end of the adaptive blade is provided and designed in particular for insertion into the pharynx and for approaching the larynx of a patient.

The first chain and the second chain each connect the proximal end and the distal end of the adaptive blade in particular directly or indirectly. The first chain and the second chain are in particular arranged approximately parallel, the distance between them decreasing from proximal to distal.

The first chain is in particular provided and designed to rest on a patient's tongue during the intended and correct use of the adaptive blade. For this purpose, the chain links of the first chain are each particularly broad and are designed with a plane or smooth or substantially smooth surface for resting on the tongue.

The first chain comprises two, three, four, five, six or more chain links. The chain links of the first chain can be identical or similar to one another. In particular, the width of the chain links of the first chain decreases from proximal to distal.

Each individual chain link of the first chain is in particular inherently stiff, i.e. is not deformable, or not appreciably deformable, under the forces and moments that occur during the intended use of the adaptive blade. Alternatively, one chain link or several chain links of the first chain can be flexible, i.e. can be elastically and/or plastically deformable under the forces and moments that occur during the intended use of the adaptive blade.

The second chain is provided, designed and arranged not to rest on the patient's tongue during the intended use of the adaptive blade. The number of the chain links of the second chain corresponds in particular to the number of the chain links of the first chain.

Each individual chain link of the second chain is in particular inherently stiff, i.e. is not deformable, or not appreciably deformable, under the forces and moments that occur during the intended use of the adaptive blade. Alternatively, one chain link or several chain links of the second chain can be flexible, i.e. can be elastically and/or plastically deformable under the forces and moments that occur during the intended use of the adaptive blade.

The adaptive blade can have one or more spacer components. In particular, the number of the spacer components is exactly as great as the number of the articulated connections between adjacent chain links of the second chain and/or exactly as great as the number of the articulated connections between adjacent chain links of the first chain. If the adaptive blade has several spacer components, these have in particular different lengths, wherein the length of the spacer components decreases from proximal to distal.

The spacer component or the spacer components can each be stiff, i.e. not deformable, or not appreciably deformable, under the forces and moments that occur during the intended use. Alternatively, the spacer component or one or more of the spacer components can be flexible, i.e. elastically and/or plastically deformable under the forces and moments that occur during the intended use of the adaptive blade. Flexibility of one or more spacer components is able to limit the force that can be transmitted to the adaptive blade or that can be exerted.

The first end of the spacer component or the first end of one of several spacer components is in particular connected in an articulated manner to an end of a chain link of the first chain or to two adjacent ends of adjacent chain links of the first chain, directly or indirectly. The second end of the spacer component or the second end of one of several spacer components is in particular connected in an articulated manner to an end of a chain link of the second chain or to two adjacent ends of two adjacent chain links of the second chain, directly or indirectly.

The adaptive blade can comprise two second chains, which are arranged substantially parallel, but with the distance between them decreasing in particular from proximal to distal. In this case, two spacer components are in particular each arranged parallel or substantially parallel and each connect one or two chain links of each of the two second chains to opposite edges of the first chain.

The two second chains and the spacer components and also the first chain are in particular arranged with mirror symmetry with respect to a plane of symmetry. In a section plane orthogonal to this plane of symmetry, the adaptive blade has a substantially U-shaped cross section.

Alternatively, the adaptive blade with a second chain or with several second chains can be asymmetrical, such that it has no mirror symmetry with respect to any plane.

Form-fit hinges are hinges that are not based on elasticity of a component or of a region of a component (for example of a film hinge) but instead on two components being guided on each other with form-fit engagement. Form-fit hinges in particular comprise roller bearings or slide bearings, with in each case two corresponding bearing surfaces which slide directly on each other or between which roller bodies are arranged.

The use of one or more form-fit hinges between chain links of the first chain and/or between chain links of the second chain and/or between the first end of a spacer component and one or more chain links of the first chain and/or between the second end of the spacer component and one or more chain links of the second chain can facilitate an articulated connection with low play and low friction between components of the adaptive blade. In this way, the blade can be adaptive in a very precisely defined manner, i.e. can adapt to the surface and deformability of the anatomy of a patient. In contrast to a conventional adaptive blade having exclusively flexure bearings or materially bonded hinges, no compromises are needed as regards the material. The chain links and the spacer component or the spacer components can be made of any desired materials, in particular also of very stiff materials with a high modulus of elasticity, of brittle materials, and of materials with a low elasticity limit.

In an adaptive blade as described here, at least some of the articulated connections are formed in particular by single-axis pivot hinges.

A single-axis pivot hinge is a hinge which has only one degree of freedom and in which one of the two components connected to each other by the pivot hinge is pivotable relative to the other component about only one predetermined pivot axis. This pivotability about the predetermined pivot axis is in particular limited to a predetermined angle range.

In particular, all of the articulated connections of the adaptive blade are formed by single-axis pivot hinges. The predetermined pivot axes of all the hinges are in particular parallel to each other or intersect at one point. In the above-described case of an adaptive blade with two second chains that are arranged with mirror symmetry with respect to a plane of symmetry, the pivot axes are in particular orthogonal to this plane of symmetry.

In an adaptive blade as described here, an articulated connection between two adjacent chain links of the first chain in particular comprises a form-fit hinge, and an articulated connection between two adjacent chain links of the second chain comprises a form-fit hinge.

In an adaptive blade as described here, several articulated connections between in each case two adjacent chain links of the first chain each in particular comprise a form-fit hinge, and several articulated connections between in each case two adjacent chain links of the second chain each comprise a form-fit hinge.

In an adaptive blade as described here, several articulated connections between spacer components and chain links of the first chain each in particular comprise a form-fit hinge.

In an adaptive blade as described here, several articulated connections between spacer components and chain links of the second chain each in particular comprise a form-fit hinge.

In an adaptive blade as described here, the form-fit hinge comprises in particular a shaft inserted into a bore in a predetermined chain link, wherein the shaft is at least either held with force-fit engagement in the bore in the predetermined chain link by an interference fit or is connected to the predetermined chain link by a weld seam.

In an adaptive blade as described here, a first chain link engages in particular in a recess in a second chain link, wherein the form-fit hinge comprises a shaft inserted into a bore in the second chain link, wherein the shaft engages through the recess in the second chain link and inside the recess through the first chain link, wherein the shaft is at least either held with force-fit engagement in the bore in the second chain link by an interference fit or is connected to the second chain link by a weld seam.

The predetermined chain link or the first chain link and the second chain link are in particular part of the first chain of the adaptive blade. Alternatively or in addition, a hinge can also be configured at the second chain of the adaptive blade.

The shaft has in particular the form of a pin which can be designed slightly conically at one end in order to facilitate its insertion into the bore during assembly of the adaptive blade. The bore is in particular a blind bore in the predetermined chain link or in the second chain link.

The interference fit comprises a portion or region of the bore in which the internal diameter of the bore prior to the insertion of the shaft, i.e. in the state free of mechanical stress, is smaller than the external diameter of the shaft in the corresponding region prior to the insertion into the bore, i.e. in the state free of mechanical stress.

The shaft is pressed into the bore during assembly, with mechanical stresses arising in the shaft and in the region surrounding the bore. The resulting restoring forces hold the shaft with force-fit engagement or frictional engagement in the bore.

In an embodiment of the adaptive blade in which the shaft engages through a recess in the second chain link and inside the recess through the adjacent first chain link, the interference fit is in particular not located near an outer surface of the second chain link. Instead, the interference fit lies in particular in a region of the bore spaced apart from the outer surface of the second chain link.

In the case of an embodiment of the bore as a blind bore with an open end and a closed end, the recess in the second chain link is in particular arranged between the open end and the closed end of the blind bore, and the interference fit is arranged between the recess and the closed end of the blind bore. The interference fit can prevent entry of dirt, in the form of a fluid or a solid, into the region of the blind bore between the recess and its closed end.

Moreover, in the case of an interference fit, a weld seam or another materially bonded join can additionally connect the shaft to the second chain link. A weld seam is provided in particular at the open end of the bore at an outer surface of the second chain link. The weld seam in particular encloses the end of the shaft in a circular shape.

In an adaptive blade as described here, chain links of the first chain are in particular substantially plate-shaped with a rectangular or trapezoidal contour.

In particular, all the chain links of the first chain are each substantially plate-shaped with a rectangular or trapezoidal contour. A trapezoidal contour of plate-shaped chain links facilitates, for example, a decreasing width of the adaptive blade from proximal to distal.

In an adaptive blade as described here, in particular at least either a chain link of the first chain or a chain link of the second chain or the spacer component has metal.

In particular, all the chain links of the first chain and/or all the chain links of the second chain and/or all the spacer components have metal. In particular, all the chain links of the first chain and/or all the chain links of the second chain and/or all the spacer components are formed from metal.

The use of metal can facilitate a high degree of stiffness of the individual chain links and spacer components and therefore a very defined deformability of the adaptive blade, i.e. a deformability defined exclusively or almost exclusively by the articulated connections. This can facilitate a more defined or better apportioned and more controlled application of force to the patient by medical personnel.

An adaptive blade as described here further comprises in particular a multi-hinge mechanism which integrates an articulated connection between two chain links of the first chain and an articulated connection between a chain link of the first chain and the spacer component.

The multi-hinge mechanism is in particular embodied with the described interference fit between a shaft and a bore into which the shaft is inserted.

In particular, the multi-hinge mechanism integrates the articulated connection between two chain links of the first chain and the articulated connection between a chain link of the first chain and the spacer component within a small installation space. The volume of the installation space of the multi-hinge mechanism is in particular not greater or not substantially greater than the sum of the volumes of two individual single hinge mechanisms. The multi-hinge mechanism in particular comprises two individual hinges, namely a hinge between two chain links of the first chain and a hinge between a chain link of the first chain and the spacer component or a hinge between the spacer component and a first chain link of the first chain and a hinge between the spacer component and a second chain link of the first chain.

A multi-hinge mechanism may be advantageous in terms of the production costs, the required installation space, the adaptive function and the mechanical robustness.

In an adaptive blade as described here, the multi-hinge mechanism in particular comprises a shaft or an axle journal with a first bearing surface and a second bearing surface, wherein the first bearing surface and the second bearing surface are constituent parts of articulated connections of the spacer component to two chain links of the first chain, or wherein the first bearing surface is a constituent part of the articulated connection between two chain links of the first chain and the second bearing surface is a constituent part of the articulated connection between a chain link of the first chain and the spacer component.

The multi-hinge mechanism further comprises in particular a third bearing surface corresponding to the first bearing surface, wherein the first bearing surface and the third bearing surface slide on each other, or several roller bodies are arranged between the first bearing surface and the third bearing surface. The multi-hinge mechanism further comprises in particular a fourth bearing surface corresponding to the second bearing surface, wherein the second bearing surface and the fourth bearing surface slide on each other, or several roller bodies are arranged between the second bearing surface and the fourth bearing surface.

The first bearing surface and the second bearing surface at the shaft or at the axle journal of the multi-hinge mechanism can be in alignment or can transition into each other and can be formed by various partial regions of a circular-cylindrical surface area of the shaft or of the axle journal. Alternatively, the first bearing surface and the second bearing surface can be separated from each other by a step for example, wherein the first bearing surface and the second bearing surface can have different degrees of curvature.

The shaft or the axle journal can be connected rigidly to a first of the chain links of the first chain. In this case, a third bearing surface corresponding to the first bearing surface is arranged at a second chain link of the first chain, and a fourth bearing surface corresponding to the second bearing surface is arranged at the spacer component. Alternatively, the shaft or the axle journal can be connected rigidly to the spacer component. In this case, the third bearing surface corresponding to the first bearing surface is arranged at a first chain link of the first chain, and the fourth bearing surface corresponding to the second bearing surface is arranged at a second chain link of the first chain.

An adaptive blade as described here further comprises in particular a multi-hinge mechanism which integrates an articulated connection between two chain links of the second chain and an articulated connection between a chain link of the second chain and the spacer component.

In particular, the multi-hinge mechanism integrates the articulated connection between two chain links of the second chain and the articulated connection between a chain link of the second chain and the spacer component within a small installation space. The volume of the installation space of the multi-hinge mechanism is in particular not greater or not substantially greater than the sum of the volumes of two individual single hinge mechanisms. The multi-hinge mechanism in particular comprises two individual hinges, namely a hinge between two chain links of the second chain and a hinge between a chain link of the second chain and the spacer component or a hinge between the spacer component and a first chain link of the second chain and a hinge between the spacer component and a second chain link of the second chain.

In an adaptive blade as described here, the multi-hinge mechanism in particular comprises a shaft or an axle journal or a pin with a first bearing surface and a second bearing surface, wherein the first bearing surface and the second bearing surface are constituent parts of articulated connections of the spacer component to two chain links of the second chain, or wherein the first bearing surface is a constituent part of the articulated connection between two chain links of the second chain and the second bearing surface is a constituent part of the articulated connection between a chain link of the second chain and the spacer component.

The multi-hinge mechanism further comprises in particular a third bearing surface corresponding to the first bearing surface, wherein the first bearing surface and the third bearing surface slide on each other, or several roller bodies are arranged between the first bearing surface and the third bearing surface. The multi-hinge mechanism further comprises in particular a fourth bearing surface corresponding to the second bearing surface, wherein the second bearing surface and the fourth bearing surface slide on each other, or several roller bodies are arranged between the second bearing surface and the fourth bearing surface.

The first bearing surface and the second bearing surface at the shaft or at the axle journal of the multi-hinge mechanism can be in alignment or can transition into each other and can be formed by various partial regions of a circular-cylindrical surface area of the shaft or of the axle journal. Alternatively, the first bearing surface and the second bearing surface can be separated from each other by a step for example, wherein the first bearing surface and the second bearing surface can have different degrees of curvature.

The shaft or the axle journal can be connected rigidly to a first of the chain links of the second chain. In this case, a third bearing surface corresponding to the first bearing surface is provided at a second chain link of the second chain, and a fourth bearing surface corresponding to the second bearing surface is provided at the spacer component. Alternatively, the shaft or the axle journal can be connected rigidly to the spacer component. In this case, the third bearing surface corresponding to the first bearing surface is arranged at a first chain link of the second chain, and the fourth bearing surface corresponding to the second bearing surface is arranged at a second chain link of the second chain.

In an adaptive blade as described here, bearing surfaces at two different chain links and a bearing surface at the spacer component are in particular arranged coaxially.

The bearing surfaces at two different chain links and the bearing surface at the spacer component are in particular at least partially arranged in each other, such that one bearing surface surrounds the two other bearing surfaces. A first of the three bearing surfaces can surround a second of the three bearing surfaces and can be surrounded by a third of the three bearing surfaces. For example, a sleeve is provided at one of the two chain links, one bearing surface being provided on the inner face and another on the outer face of the sleeve, wherein a shaft or an axle journal at a further chain link is guided in the sleeve, and the sleeve for its part is guided in a bore at the spacer component.

An adaptive blade as described here further comprises in particular corresponding abutment surfaces at two chain links connected to each other in an articulated manner, wherein the corresponding abutment surfaces are arranged such that a mechanical contact of the corresponding abutment surfaces limits a mutual pivoting movement of the chain links at which the corresponding abutment surfaces are arranged.

The corresponding abutment surfaces are in particular integrated in an articulated connection between the two chain links or are arranged in direct proximity to the articulated connection between the chain links. The corresponding abutment surfaces are in particular provided at two chain links of the first chain that are connected to each other in an articulated manner.

An adaptive blade as described here further comprises in particular corresponding abutment surfaces at a predetermined chain link and at the spacer component, wherein the corresponding abutment surfaces are arranged such that a mechanical contact of the corresponding abutment surfaces limits a pivoting movement of the predetermined chain link relative to the spacer component.

The predetermined chain link is either a chain link of the first chain or a chain link of the second chain. The predetermined chain link is in particular a chain link that is connected in an articulated manner directly to the spacer component.

Corresponding abutment surfaces that limit a pivoting movement can make the use of the adaptive blade simpler or safer, in particular during the insertion into a patient's throat. Moreover, with corresponding abutment surfaces that limit pivoting movements, it is possible to prevent a mechanical overloading of the adaptive blade, as could otherwise occur in particular in an extreme configuration of the adaptive blade.

An adaptive blade as described here further comprises in particular an elastic jacket for protecting the adaptive blade from contamination and other environmental influences.

An adaptive blade as described here further comprises in particular a channel into which at least one of an endoscope, a light source and another medical instrument can be inserted or arranged.

The channel can be composed of a plurality or a multiplicity of segments, which can each be annular or tubular and/or can each have a U-shaped cross section. In particular, each segment of the channel is arranged at a chain link or is integrated in a chain link. Alternatively or in addition, spacer components of the adaptive blade border the channel like railings.

An adaptive blade as described here further comprises in particular a handle for holding and guiding the adaptive blade.

An adaptive blade as described here can be provided and designed for repeated use and repeated sterilization (in particular steam sterilization in an autoclave) or can be provided and designed to be used just once and then disposed of.

An adaptive laryngoscope or an adaptive intubation device comprises an adaptive blade, as described here, and a handle, which is mechanically connectable or connected to the proximal end of the adaptive blade.

The adaptive laryngoscope is in particular an intubation laryngoscope and/or is provided for use in microsurgery of the larynx or for other applications in otorhinolaryngology.

BRIEF DESCRIPTION OF THE DRAWINGS

Embodiments are explained in more detail below with reference to the attached figures, in which:

FIG. 8 shows a schematic view of a part of a further adaptive blade;

FIG. 9 shows a schematic view of a cross section through the part of the adaptive blade from FIG. 8;

DETAILED DESCRIPTION

Figure 1:
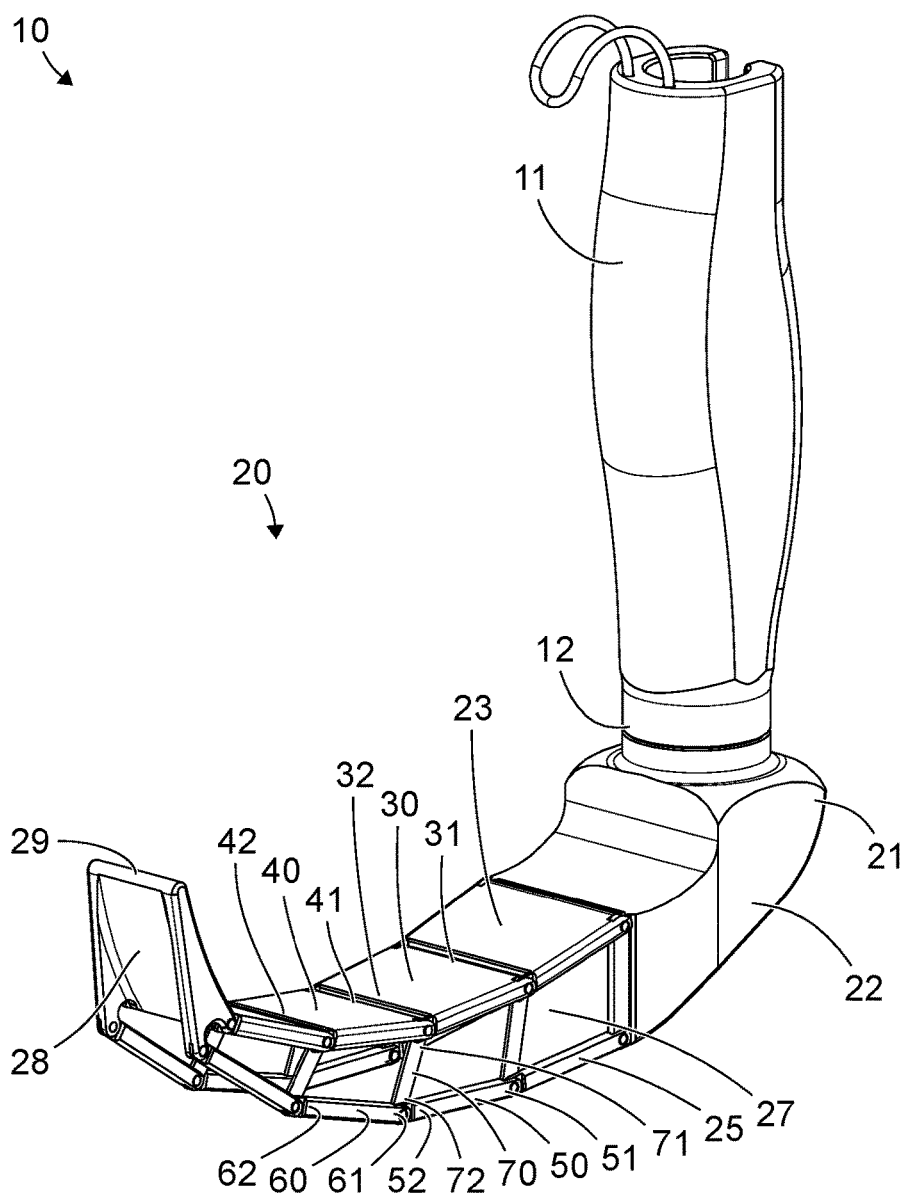
FIG. 1 shows a schematic axonometric view of an adaptive laryngoscope.

FIG. 1 shows a schematic axonometric view of an adaptive intubation laryngoscope 10 with a handle 11 for manually holding and guiding the intubation laryngoscope 10. The adaptive intubation laryngoscope 10 further comprises an adaptive blade 20 with a proximal end 21 and a distal end 29. The adaptive blade 20 has a cross section that grows smaller toward the distal end 29. The proximal end 21 of the adaptive blade 20 is mechanically connected to the handle 11 in such a way that the region of the adaptive blade 20 adjoining the proximal end encloses an angle of approximately 90 degrees (in the range between ca. 80 degrees and 120 degrees) with the handle 11.

The adaptive blade comprises a proximal endpiece 22, which forms the proximal end 21 of the adaptive blade 20. The adaptive blade further comprises a distal endpiece 28, which forms the distal end 29 of the adaptive blade 20. The adaptive blade 20 further comprises a first chain 23 and two second chains 25, which extend from the proximal endpiece 22 to the distal endpiece 28 of the adaptive blade 20.

The first chain 23 comprises several chain links 30, 40. In the example shown, the chain links 30, 40 of the first chain 23 have slightly different dimensions but are otherwise substantially similar to each other. Accordingly, by way of example, only two chain links 30, 40 of the first chain 23 are provided with reference signs.

The chain links 30, 40 of the first chain 23 are connected to each other by form-fit hinges, such that the distal end 32 of a chain link 30 is in each case connected in an articulated manner to the proximal end 41 of the distally adjacent chain link 40. The farthest proximal chain link of the first chain 23 is moreover connected to the proximal endpiece 22 of the adaptive blade 20 by a form-fit hinge. The farthest distal chain link of the first chain 23 is moreover connected to the distal endpiece 28 of the adaptive blade 20 by a form-fit hinge.

The chain links 30, 40 of the first chain 23 are each approximately or substantially plate-shaped. In the example shown, each chain link 30, 40 has a substantially trapezoidal contour. Each chain link 30, 40 has a width decreasing from proximal to distal. The width of each chain link 30 at the distal edge or end 32 thereof corresponds to the width of the distally adjacent chain link 40 at the proximal end 41 thereof. Thus, the width of the first chain 23 decreases from proximal to distal.

The widths of the proximal and distal endpieces 22, 28 of the adaptive blade 20 are equal to the widths of the first chains 23 at the proximal and distal ends thereof. Accordingly, the distal endpiece 28 has a smaller width than the proximal endpiece 22 of the adaptive blade 20.

Each of the two second chains 25 has several chain links 50, 60, which are connected to each other in pairs in an articulated manner. The chain links 50, 60 of the second chains 25 are identical to each other or substantially similar to each other. All the chain links 50, 60 of a second chain 25 or all the chain links 50, 60 of both second chains 25 can be identical to each other. Chain links 50, 60 of the second chains 25 corresponding to each other or lying opposite each other are in particular identical or mirror-symmetrical to each other. Accordingly, by way of example, only two of the chain links of the second chains 25 are provided with reference signs in FIG. 1.

The chain links 50, 60 of the second chain 25 are connected to each other in pairs by form-fit hinges, such that the distal end 52 of a chain link 50 is in each case connected in an articulated manner to the proximal end 61 of the distally adjacent chain link 60. The proximal ends of the farthest proximal chain links of the second chains 25 are each connected to the proximal endpiece 22 of the adaptive blade 20 by a form-fit hinge. The distal ends of the farthest distal chain links of the second chains 25 are each connected to the distal endpiece 28 of the adaptive blade 20 by a form-fit hinge.

The adaptive blade 20 further comprises several spacer components 70. Each spacer component 70 has a first end 71 and a second end 72. The spacer components 70 are substantially similar to each other and differ from each other particularly in terms of their lengths. Therefore, by way of example, only one spacer component 70 is provided with a reference sign.

The first end 71 of each spacer component 70 is connected to two adjacent chain links 30, 40 of the first chain 23 by a form-fit hinge. The second end 72 of each spacer component 70 is connected to two adjacent chain links 50, 60 of one of the two second chains 25 by a form-fit hinge.

The first ends 71 of the spacer components 70 are each arranged near the outer edges of the first chain 23. Two spacer components 70 are in each case arranged with mirror symmetry with respect to each other and parallel or substantially parallel to each other. Therefore, at each pair of parallel spacer components 70, the width of the arrangement of the two second chains 25 corresponds substantially to the width of the first chain 23 at the same pair of spacer components 70.

Each spacer component 70 defines with little play the distance of the distal end 32 of a first chain link 30 of the first chain 23 and of the proximal end 41 of a second chain link 40 of the first chain 23, on the one hand, from the distal end 52 of a first chain link 50 of the second chain 25 and the proximal end 61 of a second chain link 60 of the second chain 25, on the other hand. Since the lengths of the spacer components 70 decrease from proximal to distal, the distances between the first chain 23 and the second chains 25 also decrease from proximal to distal. As is indicated in FIG. 1, this has the effect that a movement of the chains 23, 25 in a central region in one direction (downward in FIG. 1) entails a pivoting movement of the distal end 29 of the adaptive blade 20 in the opposite direction (upward in FIG.

1). This can facilitate a shaping of the adaptive blade 20 to a patient's tongue and a distribution of a force applied to a patient's tongue.

The chain links 30, 40 of the first chain 23, the chain links 50, 60 of the second chain 25 and the spacer components 70 together have a configuration with a substantially rectangular U-shaped cross section, wherein the spacer components 70 and the second chains 25 do not form closed side walls, but only structures akin to fences. A space inside the U-shaped cross section forms a channel 27 through which a light source, a camera, an endoscope or another medical instrument can be partially or completely guided, or in which a light source, a camera, an endoscope or another medical instrument can be arranged.

Figure 2:
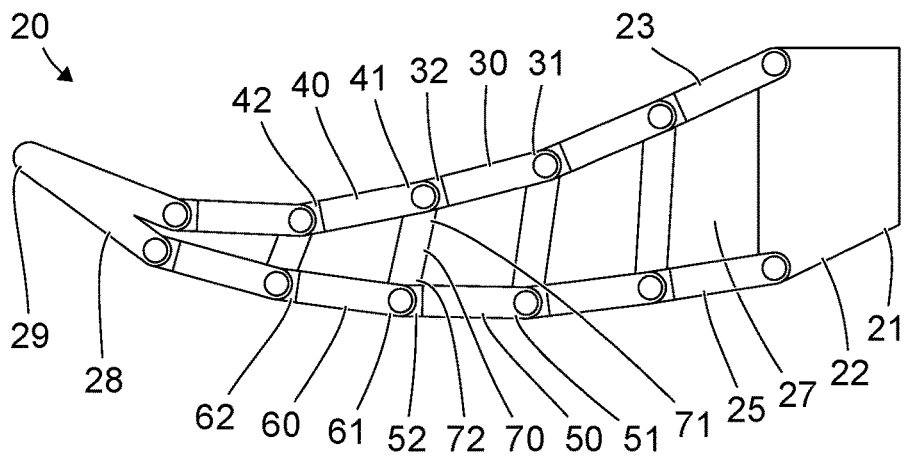
FIG. 2 shows a schematic view of an adaptive blade for a laryngoscope.

FIG. 2 shows a schematic view of an adaptive blade 20 which, in terms of certain features, properties and functions, is similar to the adaptive blade 20 of the laryngoscope shown in FIG. 1. The blade 20 shown in FIG. 2 is provided and designed in particular for releasable or permanent mechanical connection to a handle in order to form a laryngoscope.

In FIG. 2, small circles indicate the form-fit hinges between the chain links 30, 40 of the first chain 23, the ends 71, 72 of the spacer components 70 and the chain links 50, 60 of the second chain 25. The pivot axes and axes of symmetry 88, 98 of all of the form-fit hinges are orthogonal to the drawing plane of FIG. 2.

Figure 3:
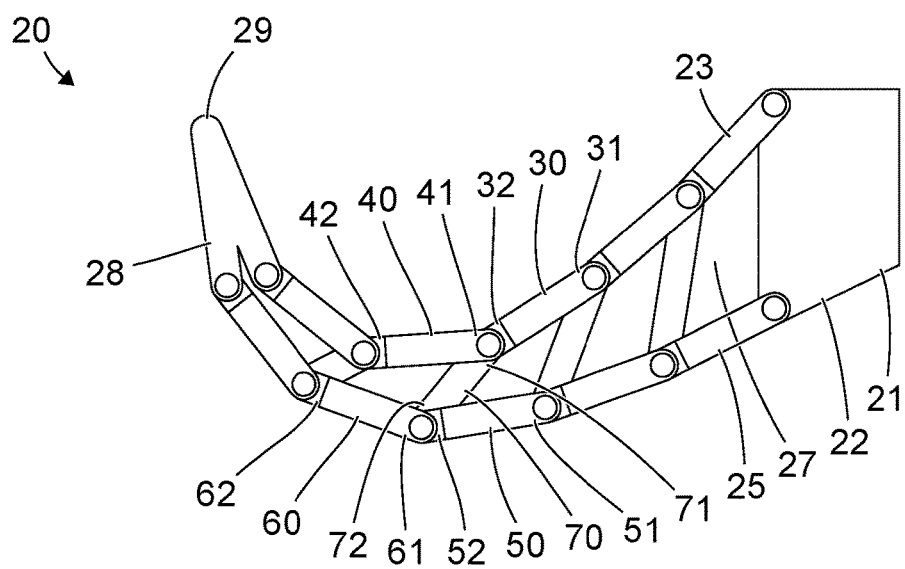
FIG. 3 shows a further schematic view of the adaptive blade from FIG. 2.

FIG. 3 shows a further schematic view of the adaptive blade 20 from FIG. 2. The drawing plane of FIG. 3 corresponds to the drawing plane of FIG. 2.

In FIG. 3, the adaptive blade 20 is shown in a configuration or situation that differs from the situation shown in FIG. 2. The configuration shown in FIG. 3 arises, for example, by shaping the adaptive blade 20 to the curved surface of a patient's tongue. Chain links 30, 40, 50, 60 in a central region of the chains 23, 25 in this case yield in one direction (downward in FIG. 3), while the distal endpiece 28 of the adaptive blade 20 is pivoted in the opposite direction (upward in FIG. 3).

Figure 4:
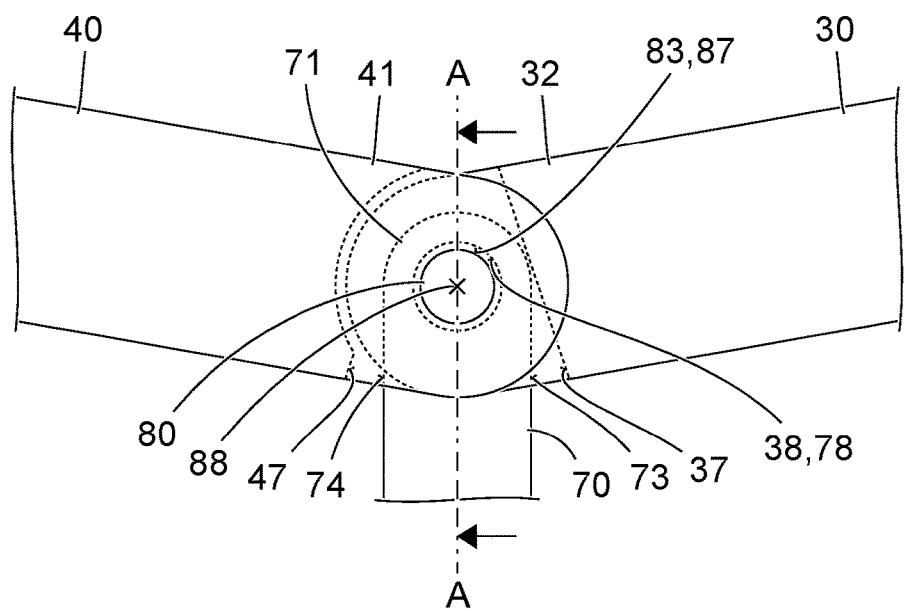
FIG. 4 shows a schematic view of a part of an adaptive blade.

FIG. 4 shows a schematic view of a part of an adaptive blade as has been described with reference to FIGS. 1 to 3. The drawing plane of FIG. 4 is parallel to the drawing planes of FIGS. 2 and 3.

FIG. 4 shows the articulated connection between the distal end 32 of a first chain link 30, the proximal end 41 of a second chain link 40 and a first end 71 of a spacer component 70. The second chain link 40 partially hides the first chain link 30 and the spacer component 70. Contours of the first chain link 30 and of the spacer component 70 are indicated by broken lines, insofar as they are hidden and therefore not actually visible. Further structures not actually visible in the view in FIG. 4 are also indicated by broken lines.

The articulated connection of the chain links 30, 40 and of the spacer component 70 is provided by a shaft 80 with a circular-cylindrical cross section. The shaft 80 has an axis of symmetry 88, which forms the pivot axis of the articulated connection. The end of the shaft 80 facing toward the observer is inserted into a corresponding bore in the second chain link 40 and is joined to the latter by frictional engagement and/or material bonding. Ring-shaped regions of the surface of the shaft 80 form bearing surfaces 83, 87. A bearing surface 38 corresponding to the bearing surface 83, in particular lying opposite the latter, is provided at the first chain link 30. A bearing surface 78 corresponding to the bearing surface 87 at the shaft 80, in particular lying opposite the bearing surface 87, is provided at the spacer component 70. FIG. 4 indicates a space between corresponding bearing surfaces 83, 38 and 87, 78, which space allows movements with little friction. In contrast to what is shown in FIG. 4, roller bodies can be provided between the corresponding bearing surfaces 83, 38 and/or between the corresponding bearing surfaces 87, 78.

An abutment surface 37 is provided at the first chain link 30. A first abutment surface 73 corresponding to the abutment surface 37 at the first chain link 30 is provided at the spacer component 70. A mechanical contact between the corresponding abutment surfaces 37, 73 at the first chain link 30 and at the spacer component 70 limits a pivoting movement of the spacer component 70 relative to the first chain link 30.

An abutment surface 47 is provided at the second chain link 40. A second abutment surface 74 corresponding to the abutment surface 47 at the second chain link 40 is provided at the spacer component 70. A mechanical contact between the abutment surfaces 47, 74 at the second chain link 40 and at the spacer component 70 limits a pivoting movement of the second chain link 40 relative to the spacer component 70.

Figure 5:
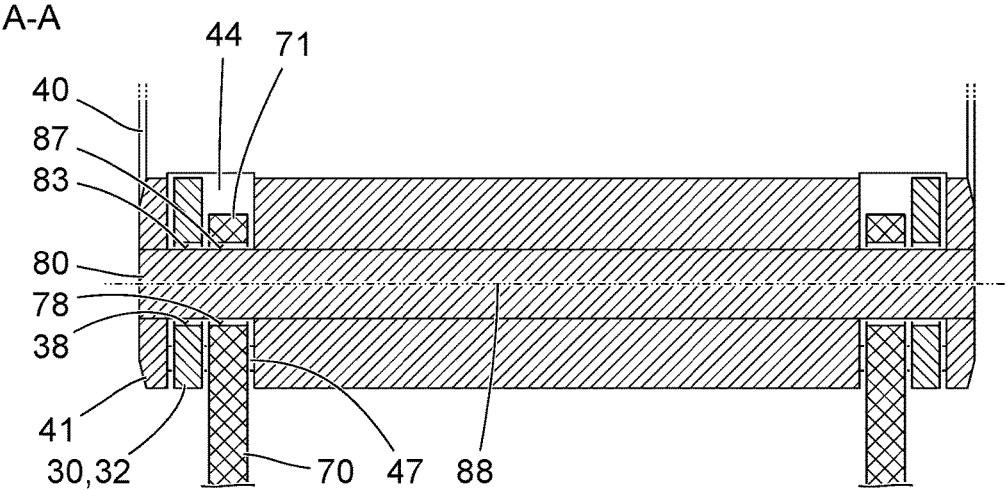
FIG. 5 shows a schematic view of a cross section through the part of the adaptive blade from FIG. 4.

FIG. 5 shows a schematic view of a cross section, along the section plane A-A indicated in FIG. 4, through the articulated connection, shown in FIG. 4, of the chain links 30, 40 and of the spacer component 70. The section plane A-A of FIG. 5 is orthogonal to the drawing plane of FIG. 4 and contains the pivot axis and axis of symmetry 88 of the first shaft 80.

The section plane A-A of FIG. 5 intersects the distal end 32 of the first chain link 30, the proximal end 41 of the second chain link 40 and two spacer components 70. The chain links 30, 40 are mirror-symmetrical with respect to a plane of symmetry, which is orthogonal to the section plane A-A of FIG. 5 and to the axis of symmetry 88 of the shaft 80. The spacer components 70 are mirror-symmetrical with respect to the same plane of symmetry. Therefore, reference signs are provided only at one side (the left-hand side in FIG. 5).

The proximal end 41 of the second chain link 40 has two recesses 44. The distal end 32 of the first chain link 30 is formed by two tongue-shaped or slat-like continuations, which engage in the recesses 44 at the proximal end 41 of the second chain link 40. Moreover, one end of a spacer component 70 engages in each recess 44 in the proximal end 41 of the second chain link 40.

The shaft 80 is inserted with little play, in particular with frictional engagement, into a corresponding bore in the proximal end 41 of the second chain link 40. The recesses 44 in the proximal end 41 of the second chain link 40 are arranged such that the shaft 80 passes through both recesses 44. Partial regions of the outer surface of the shaft 80 that form the bearing surfaces 83, 87 lie open in the recesses 44. The tongues or slats forming the distal end 32 of the first chain link 30 each have a bore through which the shaft 80 engages, the inner surfaces of which bore form bearing surfaces 38 corresponding to the bearing surfaces 83 at the shaft 80. The ends 71 of the spacer components 70 each have a bore through which the shaft 80 engages, the inner surfaces of which bore form bearing surfaces 78 corresponding to the bearing surfaces 87 at the shaft 80.

Identical hatching indicates that, in the example shown in FIGS. 4 and 5, the shaft 80 is rigidly connected to the proximal end 41 of the second chain link 40 and to this extent forms a part of the second chain link 40. The bearing surfaces 38 at the distal end 32 of the first chain link 30 and the corresponding bearing surfaces 83 at the shaft 80 provide a form-fit hinge between the first chain link 30 and the second chain link 40. The bearing surfaces 78 at the spacer components 70 and the corresponding bearing surfaces 87 at the shaft 80 provide form-fit hinges between the second chain link 40 and the spacer components 70.

The regions of the shaft 80 inside the recesses 44 in the proximal end 41 of the second chain link 40, the bearing surfaces 83, 87 located thereon, and the corresponding bearing surfaces 38, 78 at the distal end 32 of the first chain link 30 and at the end 71 of the spacer component 70 form a multi-hinge mechanism. This multi-hinge mechanism brings together, within a small installation space, form-fit hinges between both chain links 30, 40 and the spacer component 70.

Figure 6:
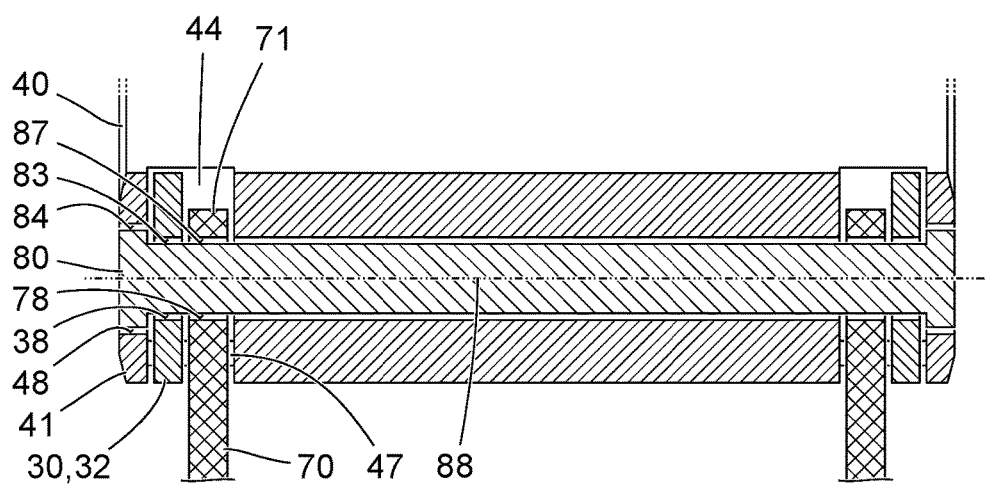
FIG. 6 shows a schematic view of a cross section through a part of a further adaptive blade.

FIG. 6 shows a schematic view of a cross section through an alternative embodiment of an articulated connection between chain links 30, 40 and a spacer component 70 of an adaptive blade as shown in FIGS. 1 to 3. The nature of the view, in particular the section plane, corresponds to that of FIG. 5. In terms of certain features, properties and functions, the embodiment shown in FIG. 6 is similar to the embodiment shown in FIGS. 4 and 5. The features, properties and functions that distinguish the embodiment shown in FIG. 6 from the embodiment shown in FIGS. 4 and 5 are in particular described below.

In the articulated connection shown in FIG. 6, the shaft 80 is not connected rigidly to the second chain link 40. Instead, the shaft 80 and the corresponding bore in the proximal end 41 of the second chain link 40 are designed such that the shaft 80 is not held with frictional engagement and instead bearing surfaces 48 are formed. Bearing surfaces 84 corresponding to the bearing surfaces 48 at the proximal end 41 of the second chain link 40 are formed at the shaft 80. In FIG. 6, a bearing play between the corresponding bearing surfaces 48, 84 indicates a rotatability of the shaft 80 relative to the second chain link 40. The shaft 80 can thus rotate relative to the spacer component 70 and the distal end 32 of the first chain link 30 and also relative to the proximal end 41 of the second chain link 40.

A form-fit hinge between the chain links 30, 40 is thus formed by the bearing surfaces 38 at the distal end 32 of the first chain link 30, the corresponding bearing surfaces 83 at the shaft 80, the bearing surfaces 48 at the proximal end 41 of the second chain link 40, and the corresponding bearing surfaces 84 at the shaft 80. All the other articulated connections are also formed accordingly via the shaft 80.

To prevent the shaft 80 from sliding out of the bores in the chain links 30, 40 and in the spacer components 70 as a result of a movement parallel to the axis of symmetry 88 of the shaft 80, the ends of the shaft 80 in the example shown each have an enlarged diameter.

Figure 7:
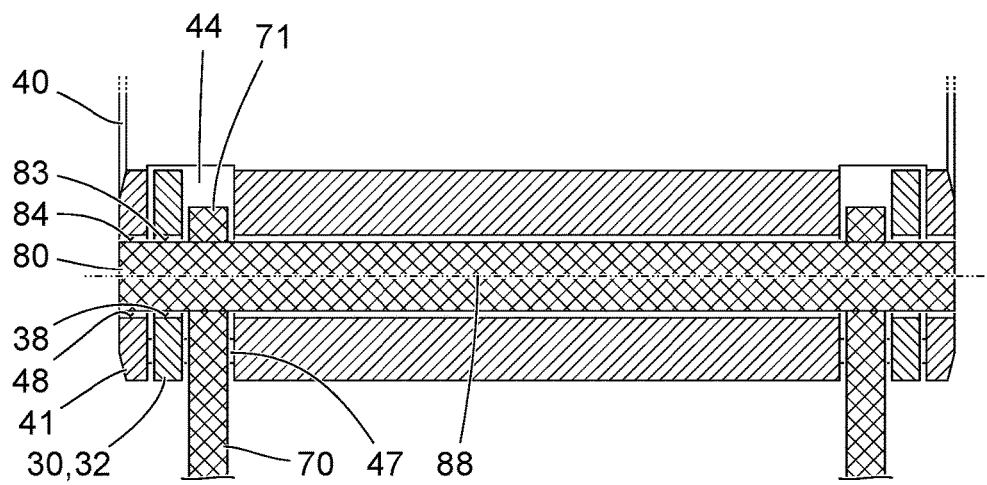
FIG. 7 shows a schematic view of a cross section through a part of a further adaptive blade.

FIG. 7 shows a schematic view of a cross section through a further embodiment of an articulated connection between chain links 30, 40 and spacer components 70, which articulated connection, in terms of certain features, properties and functions, is similar to the articulated connections shown in FIGS. 4 to 6. The nature of the view, in particular the section plane, corresponds to that of FIGS. 5 and 6. The features, properties and functions that distinguish the embodiment shown in FIG. 7 from the embodiments shown in FIGS. 4 to 6 are described below.

In the articulated connection shown in FIG. 7, the shaft 80 is connected to the spacer components 70 by frictional or force-fit engagement and/or by material bonding. The shaft 80 is to this extent a constituent part of the spacer components 70 and connects the spacer components rigidly to each other. This is indicated by the hatching of the sectional surfaces in FIG. 7. The rigid connection of the spacer components 70 can increase the stiffness of the whole adaptive blade.

In the articulated connection shown in FIG. 7, the bearing surface 38 at the distal end 32 of the first chain link 30 and the corresponding bearing surfaces 83 at the shaft 80 constitute form-fit hinges between the first chain link 30 and the spacer components 70. Bearing surfaces 48 at the proximal end 41 of the second chain link 40 and corresponding bearing surfaces 84 at the shaft 80 provide form-fit hinges between the proximal end 41 of the second chain link 40 and the spacer components 70. The bearing surfaces 83, 84 at the shaft 80 and the corresponding bearing surfaces 38, 48 at the chain links 30, 40 together form multi-hinge mechanisms, which simultaneously form articulated connections between the chain links 30, 40.

FIG. 8 shows a schematic view of an alternative embodiment of an articulated connection between chain links 30, 40 and a spacer component 70 of an adaptive blade as shown in FIGS. 1 to 3. The nature of the view in FIG. 8 corresponds to that of FIG. 4. In terms of certain features, properties and functions, the embodiment shown in FIG. 8 is similar to the embodiments shown in FIGS. 4 to 7. The features, properties and functions that distinguish the embodiment shown in FIG. 8 from the embodiments shown in FIGS. 4 to 7 are in particular described below.

The embodiment shown in FIG. 8 differs from the embodiment shown in FIGS. 4 and 5 particularly in that an abutment surface 34 is provided at the distal end 32 of the first chain link 30 and a corresponding abutment surface 43 is provided at the proximal end 41 of the second chain link 40. A mechanical contact between the corresponding abutment surfaces 34, 43 at the first chain link 30 and at the second chain link limits a pivoting movement of the chain links 30, 40 relative to each other.

In the embodiment shown in FIG. 8, no abutment surface is provided at the spacer component 70. Alternatively, and in contrast to the view in FIG. 8, further abutment surfaces can be provided in addition to the abutment surfaces 34, 43, the mechanical contact of which further abutment surfaces limits a movement of the spacer component 70 relative to one or both of the chain links 30, 40. In other words, the abutment surfaces 47, 74 shown in FIG. 4, for directly limiting a relative movement of spacer component 70 and chain links 30, 40, and the abutment surfaces 34, 43 shown in FIG. 8, for directly limiting a relative movement of the chain links 30, 40, can be provided simultaneously at one multi-hinge mechanism.

FIG. 9 shows a schematic view of a cross section, along the section plane B-B indicated in FIG. 8, through the articulated connection, shown in FIG. 8, of the chain links 30, 40 and of the spacer component 70. The section plane B-B of FIG. 9 is orthogonal to the drawing plane of FIG. 8 and contains the pivot axis 88.

It will be seen from FIG. 8 that the embodiment shown there also differs from the embodiment shown in FIGS. 4 and 5 in that two short shafts 81 are provided, instead of one continuous shaft extending across the whole width of the second chain link 40. Each of the short shafts 81 has the form of a pin with a conical region 82. The pivot axis 88 is at the same time the axes of symmetry of the shafts 81.

The second chain link 40 has two blind bores 49 arranged with mirror symmetry to each other and facing away from each other. Each of the short shafts 81 is inserted into one of the two blind bores 49 such that the conical region 82 of the shaft 81 is directed toward the closed end of the blind bore 49. During assembly of the adaptive blade, the conical regions 82 of the shafts 81 facilitate the insertion of the shafts 81 into the blind bores 49.

In a manner similar to the embodiments shown in FIGS. 4 to 7, the shafts 81 engage through the recesses 44 in the proximal end 41 of the second chain link. Surface regions of the shafts 81 inside the recesses 44 form bearing surfaces 83, 87 having the described functions. Each recess 44 is arranged between the open end and the closed end of the associated blind bore 49 and between the ends of the associated shaft 81.

Each shaft 81 is held with force-fit engagement or frictional engagement in the associated blind bore 49 by means of an interference fit. The interference fit comprises a portion or region of the blind bore 49 in which the internal diameter of the blind bore 49 prior to the insertion of the shaft 81 (i.e. in the state free of mechanical stress) is smaller than the external diameter of the shaft 81 in the corresponding region prior to the insertion into the blind bore 49 (i.e. in the state free of mechanical stress). Upon insertion of the shafts 81 into the blind bores 49, this leads to deformations and mechanical stresses in the shafts 81 and in the regions surrounding the blind bores 49. The resulting restoring forces hold the shafts 81 with force-fit engagement or frictional engagement in the blind bores 49. This interference fit is in each case located in a region between the recess 44 and the closed end of the blind bore 49.

In addition, each shaft 81 is materially bonded to the proximal end 41 of the second chain link 40 by a circular weld seam 89. The circular weld seams 89 are provided at the open ends of the blind bores 49. The ends of the shafts 81 at the weld seams 89, the surrounding surface regions of the second chain link 40, and the weld seams 89 are in particular flat or ground to a plane finish and/or polished.

Alternatively, and in contrast to what is shown in FIGS. 8 and 9, each shaft 81 can be joined to the second chain link 40 by only one of an interference fit and a weld seam 89. Moreover, in contrast to what is shown in FIGS. 8 and 9, and as an alternative or an addition to the weld seam 89 and/or to the interference fit, each shaft 81 can be mechanically connected to the second chain link 40 or to the first chain link 30 by screw threads or in some other way involving form-fit engagement, material bonding, force-fit engagement or frictional engagement.

In contrast to what is shown in FIGS. 8 and 9, it is possible, in an embodiment with the abutment surfaces 34, 43 shown in FIG. 8 for limiting the relative movement of the chain links 30, 40, to replace two short shafts 81 with one continuous shaft, as has been described with reference to FIGS. 4 to 7.

In contrast to what is shown in FIGS. 8 and 9, it is possible, in an embodiment with the two short shafts 81 shown in FIG. 8, that the abutment surfaces 34, 43 (for limiting the relative movement of the chain links 30, 40) are replaced by or complemented with abutment surfaces 37, 73, 47, 74 for limiting the movement of the spacer component 70 relative to the chain links 30, 40.

Articulated connections between the chain links 50, 60 of the second chain 25 and the second ends 72 of the spacer components 70 of the adaptive blade 20 (cf. FIGS. 1 to 3) can be of a similar design to the form-fit hinges shown in FIGS. 4 to 9 between the chain links 30, 40 of the first chains 23 and the first ends 71 of the spacer components 70. In particular, however, no abutment surfaces are provided at the articulated connections between the chain links 50, 60 of the second chain 25 and the second ends 72 of the spacer components 70, or at least no abutment surfaces that are effective during the intended use of the adaptive blade 20. Alternatively, corresponding pairs of abutment surfaces can be provided also at the articulated connections between the chain links 50, 60 of the second chain 25 and the second ends 72 of the spacer components 70, in order to limit relative movements.

Figure 10:
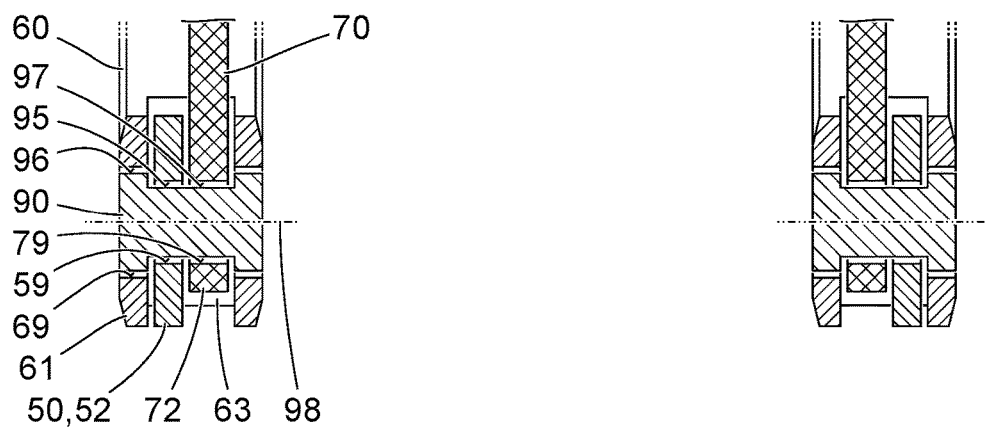
FIG. 10 shows a schematic view of a cross section through a further part of an adaptive blade.

FIG. 10 shows a schematic view of a cross section through articulated connections between chain links 50, 60 of second chains 25 and spacer components 70 of an adaptive blade 20 (cf. FIGS. 1 to 3). Since the second chains, formed by the chain links 50, 60, and the spacer components 70 are arranged with mirror symmetry, only one chain (namely the left-hand chain) and the left-hand spacer component 70 are provided with reference signs in FIG. 10.

Recesses 63 are provided in the proximal ends 61 of the second chain links 60. Bores in which second shafts 90 are arranged are provided in the distal ends 52 of the first chain links 50 and in the proximal ends 61 of the second chain links 60 and in the ends 72 of the spacer components 70. The second shafts 90 extend through the recesses 63 in the proximal ends 61 of the second chain links 60. The second shafts 90 lie free inside the recesses 63 and extend through the bores in the distal ends 52 of the first chain links and in the ends 72 of the spacer components 70. Inner faces of the bores form bearing surfaces 59, 69, 79, and, lying opposite these, surface regions of the second shafts 90 form corresponding bearing surfaces 95, 96, 97.

The bearing surface 59 at the distal ends 52 of the first chain links 50, the corresponding bearing surfaces 95 at the second shafts 90, the bearing surfaces 69 at the proximal ends 61 of the second chain links 60, and the corresponding bearing surfaces 96 at the second shafts 90 provide form-fit hinges between the chain links 50, 60. The bearing surfaces 59 at the distal ends 52 of the first chain links 50, the corresponding bearing surfaces 95 at the second shafts 90, the bearing surfaces 79 at the spacer components 70, and the corresponding bearing surfaces 97 at the second shafts 90 provide form-fit hinges between the first chain links 50 and the spacer components 70. The bearing surfaces 69 at the proximal ends 61 of the second chain links 60, the corresponding bearing surfaces 96 at the second shafts 90, the bearing surfaces 79 at the ends 72 of the spacer components 70, and the corresponding bearing surfaces 97 at the second shafts 90 provide form-fit hinges between the second chain links 60 and the spacer components 70.

In contrast to what is shown in FIG. 10, the second shafts 90 can be connected to the second chain links 60, for example analogously to the articulated connection shown in FIGS. 4 and 5, or can be connected rigidly to the spacer components 70 or connected rigidly to the distal ends 52 of the first chain links 50, analogously to the articulated connection shown in FIG. 7.

Figure 11:
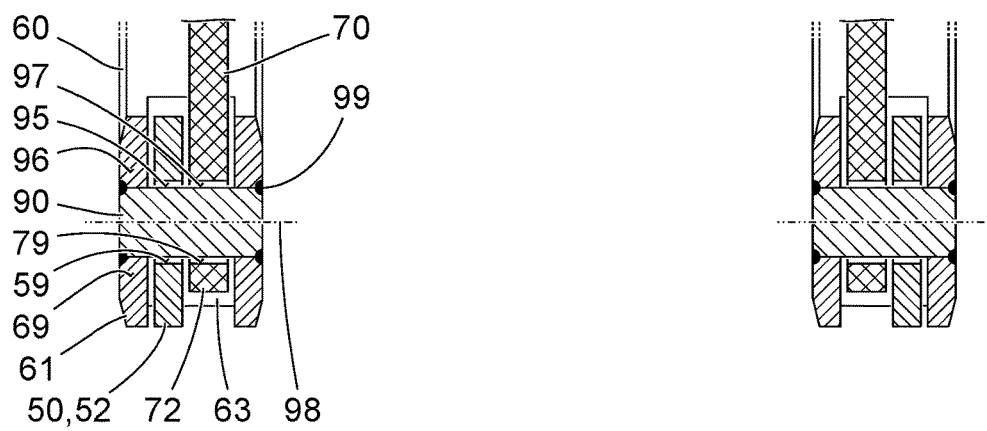
FIG. 11 shows a schematic view of a cross section through a further part of a further adaptive blade.

FIG. 11 shows a schematic view of a cross section through an alternative embodiment of the articulated connections between chain links 50, 60 of second chains 25 and spacer components 70 of an adaptive blade 20 (cf. FIGS. 1 to 3), which embodiment is similar, in terms of certain features, properties and functions, to the embodiment shown in FIG. 10. The nature of the view, in particular the indicated section plane, corresponds to that of FIG. 10. The features, properties and functions that distinguish the embodiment shown in FIG. 11 from the embodiment shown in FIG. 10 are in particular described below.

In the embodiment shown in FIG. 11, the shafts 90 are joined to the proximal ends 61 of the second chain links 60 by weld seams 99. The weld seams 99 are each circular. At each end of each shaft 90, a weld seam 99 is provided that encloses the end. The ends of the shafts 90 at the weld seams 99, the surrounding surface regions of the second chain links 60, and the weld seams 99 are in particular flat or ground to a plane finish and/or polished.

In contrast to what is shown in FIG. 11, it is possible to provide only one weld seam 99 on each shaft 90. In contrast to what is shown in FIG. 11, and as an alternative or in addition to one or both weld seams 99, each shaft 90 can be joined to the proximal end 61 of the second chain link 60 in another way.

In contrast to what is shown in FIGS. 4 to 11, each shaft 80, 81, 90 can be joined to the distal end 32, 52 of the first chain link 30, 50 instead of to the proximal end 41, 61 of the distally adjacent second chain link.

REFERENCE SIGNS 10 laryngoscope
11 handle of the laryngoscope 10
12 distal end of the handle 11 of the laryngoscope 10
20 adaptive blade of the laryngoscope 10
21 proximal end of the adaptive blade 20
22 proximal endpiece of the adaptive blade 20
23 first chain of the adaptive blade 20
25 chain of the adaptive blade 20
27 channel for a medical instrument at the adaptive blade 20
28 distal endpiece of the adaptive blade 20
29 distal end of the adaptive blade 20
30 first chain link of the first chain 23 of the adaptive blade 20
31 proximal end of the first chain link 30 of the first chain 23
32 distal end of the first chain link 30 of the first chain 23
34 abutment surface at the first chain link 30 of the first chain 23, corresponding to the abutment surface 43 at the second chain link 40 of the first chain 23
37 abutment surface at the first chain link 30 of the first chain 23, corresponding to the abutment surface 73 at the spacer component 70
38 bearing surface at the first chain link 30 of the first chain 23, corresponding to the bearing surface 83 at the first shaft 80
40 second chain link of the first chain 23 of the adaptive blade 20
41 proximal end of the second chain link 40 of the first chain 23
42 distal end of the second chain link 40 of the first chain 23
43 abutment surface at the second chain link 40 of the first chain 23, corresponding to the abutment surface 34 at the first chain link 30 of the first chain 23
44 recess at the proximal end 41 of the second chain link 40
47 abutment surface at the second chain link 40 of the first chain 23, corresponding to the abutment surface 74 at the spacer component 70
48 bearing surface at the second chain link 40 of the first chain 23, corresponding to the bearing surface 84 at the first shaft 80
49 blind bore in the second chain link 40
50 first chain link of the second chain 25 of the adaptive blade 20
51 proximal end of the first chain link 50 of the second chain 25
52 distal end of the first chain link 50 of the second chain 25
59 bearing surface at the first chain link 50 of the second chain 25, corresponding to the bearing surface 95 at the second shaft 90
60 second chain link of the second chain 25 of the adaptive blade 20
61 proximal end of the second chain link 60 of the second chain 25
62 distal end of the second chain link 60 of the second chain 25
63 recess at the proximal end 61 of the second chain link 60
69 bearing surface at the second chain link 60 of the second chain 25, corresponding to the bearing surface 96 at the second shaft 90
70 spacer component of the adaptive blade 20
71 first end of the spacer component 70
72 second end of the spacer component 70
73 first abutment surface at the spacer component 70, corresponding to the abutment surface 37 at the first chain link 30 of the first chain 23
74 second abutment surface at the spacer component 70, corresponding to the abutment surface 47 at the second chain link 40 of the first chain 23
78 bearing surface at the spacer component 70, corresponding to the bearing surface 87 at the first shaft 80
79 bearing surface at the spacer component 70, corresponding to the bearing surface 97 at the second shaft 90
80 first shaft for the articulated connection of two chain links 30, 40 of the first chain 23 and of the first end 71 of a spacer component 70
81 pin as shaft for the articulated connection of two chain links 30, 40 of the first chain 23 and of the first end 71 of a spacer component 70, inserted into the blind hole 49
82 conical region at one end of the pin 81
83 bearing surface at the first shaft 80, corresponding to the bearing surface 38 at the first chain link 30 of the first chain 23
84 bearing surface at the first shaft 80 or at the pin 81, corresponding to the bearing surface 48 at the second chain link 40 of the first chain 23
87 bearing surface at the first shaft 80 or at the pin 81, corresponding to the bearing surface 78 at the spacer component 70
88 axis of symmetry of the first shaft 80 or of the pin 81, and pivot axis
89 circular weld seam between second chain link 40 of the first chain 23 and pin 81
90 second shaft or pin for the articulated connection of two chain links 50, 60 of the second chain 25 and of the second end 72 of a spacer component 70
95 bearing surface at the second shaft 90, corresponding to the bearing surface 59 at the first chain link 50 of the second chain 25
96 bearing surface at the second shaft 90, corresponding to the bearing surface 69 at the second chain link 60 of the second chain 25
97 bearing surface at the second shaft 90, corresponding to the bearing surface 79 at the spacer component 70
98 axis of the second shaft 90 and pivot axis
99 circular weld seam between second chain link 60 of the second chain 25 and second shaft 90

The invention claimed is:

1. An adaptive blade for a laryngoscope, comprising:
a proximal end;
a distal end;
a first chain arranged between the proximal end and the distal end of the adaptive blade and composed of a plurality of similar chain links which are each connected in pairs in an articulated manner;
a second chain arranged between the proximal end and the distal end of the adaptive blade and composed of a plurality of similar chain links which are each connected in pairs in an articulated manner;

a spacer component, wherein a first end of the spacer component is connected in an articulated manner to one of the chain links of the first chain, and wherein a second end of the spacer component is connected in an articulated manner to one of the chain links of the second chain, wherein one of the articulated connections between the chain links of the first chain and the spacer component comprises a form-fit hinge, and one of the articulated connections between the chain links of the second chain and the spacer component comprises a form-fit hinge, the adaptive blade having a plurality of spacer components, the first end of each spacer component of the plurality of spacer components being connected in an articulated manner to two adjacent chain links of the plurality of chain links of the first chain, the second end of each spacer component of the plurality of spacer components being connected in an articulated manner to two adjacent chain links of the plurality of chain links of the second chain, the length of the spacer components measured in each case between the first end and the second end decreases from the proximal end of the blade to the distal end of the blade.

2. The adaptive blade according to claim 1, wherein
an articulated connection between two adjacent chain links of the first chain comprises a form-fit hinge,
an articulated connection between two adjacent chain links of the second chain comprises a form-fit hinge.

3. The adaptive blade according to claim 1, wherein
several articulated connections between in each case two adjacent chain links of the first chain each comprise a form-fit hinge,
several articulated connections between in each case two adjacent chain links of the second chain each comprise a form-fit hinge.

4. The adaptive blade according to claim 1, wherein several articulated connections between the spacer components and the chain links of the first chain each comprise a form-fit hinge.

5. The adaptive blade according to claim 1, wherein
a first chain link engages in a recess in a second chain link,
the form-fit hinges comprise a shaft inserted into a bore in the second chain link,
the shaft engages through the recess in the second chain link and inside the recess through the first chain link,
the shaft is at least either held with force-fit engagement in the bore in the second chain link by an interference fit or is connected to the second chain link by a weld seam.

6. The adaptive blade according to claim 1, wherein chain links of the first chain are substantially plate-shaped with a rectangular or trapezoidal contour.

7. The adaptive blade according to claim 1, wherein at least one of a chain link of the first chain or a chain link of the second chain or the spacer component has metal.

8. The adaptive blade according to claim 1, further comprising:
a multi-hinge mechanism which integrates an articulated connection between two chain links of the first chain and an articulated connection between a chain link of the first chain and the spacer component.

9. The adaptive blade according to claim 8, wherein the multi-hinge mechanism comprises a shaft or an axle journal or a pin with a first bearing surface and a second bearing surface, and
wherein the first bearing surface and the second bearing surface are constituent parts of articulated connections of the spacer component to two chain links of the first chain.

10. The adaptive blade according to claim 8, wherein bearing surfaces at two different chain links and a bearing surface at the spacer component are arranged coaxially.

11. The adaptive blade according to claim 8, wherein the first bearing surface is a constituent part of the articulated connection between two chain links of the first chain and the second bearing surface is a constituent part of the articulated connection between a chain link of the first chain and the spacer component.

12. The adaptive blade according to claim 1, further comprising:
corresponding abutment surfaces at two chain links connected to each other in an articulated manner;
wherein the corresponding abutment surfaces are arranged such that a mechanical contact of the corresponding abutment surfaces limits a pivoting movement of the two adjacent chain links relative to each other.

13. The adaptive blade according to claim 1, wherein a distance between the first chain and the second chain decreases from the proximal end to the distal end.

14. The adaptive blade according to claim 1, wherein the plurality of similar chain links of the first chain are identical and wherein the plurality of similar chain links of the second chain are identical.

15. An adaptive laryngoscope or adaptive intubation device, comprising:
an adaptive blade including:
a proximal end;
a distal end;
a first chain arranged between the proximal end and the distal end of the adaptive blade and composed of a plurality of similar chain links which are each connected in pairs in an articulated manner;
a second chain arranged between the proximal end and the distal end of the adaptive blade and composed of a plurality of similar chain links which are each connected in pairs in an articulated manner;
a spacer component, wherein a first end of the spacer component is connected in an articulated manner to one of the chain links of the first chain, and wherein a second end of the spacer component is connected in an articulated manner to one of the chain links of the second chain,
wherein one of the articulated connections between the chain links of the first chain and the spacer component comprises a form-fit hinge, and one of the articulated connections between the chain links of the second chain and the spacer component comprises a form-fit hinge; and
a handle, which is mechanically connectable or connected to the proximal end of the adaptive blade, wherein a distance between the first chain and the second chain decreases from the proximal end to the distal end.

16. The adaptive laryngoscope or adaptive intubation device according to claim 15, wherein the plurality of similar chain links of the first chain are identical and wherein the plurality of similar chain links of the second chain are identical.

17. An adaptive blade for a laryngoscope, comprising:
a proximal end;
a distal end;

a first chain arranged between the proximal end and the distal end of the adaptive blade and composed of a plurality of similar chain links which are each connected in pairs in an articulated manner;

a second chain arranged between the proximal end and the distal end of the adaptive blade and composed of a plurality of similar chain links which are each connected in pairs in an articulated manner;

a spacer component, wherein a first end of the spacer component is connected in an articulated manner to one of the chain links of the first chain, and wherein a second end of the spacer component is connected in an articulated manner to one of the chain links of the second chain, wherein one of the articulated connections between the chain links of the first chain and the spacer component comprises a form-fit hinge, and one of the articulated connections between the chain links of the second chain and the spacer component comprises a form-fit hinge, wherein chain links of the first chain are substantially plate-shaped with a rectangular or trapezoidal contour.

18. An adaptive blade for a laryngoscope, comprising:

a proximal end;

a distal end;

a first chain arranged between the proximal end and the distal end of the adaptive blade and composed of a plurality of similar chain links which are each connected in pairs in an articulated manner;

a second chain arranged between the proximal end and the distal end of the adaptive blade and composed of a plurality of similar chain links which are each connected in pairs in an articulated manner;

a spacer component, wherein a first end of the spacer component is connected in an articulated manner to one of the chain links of the first chain, and wherein a second end of the spacer component is connected in an articulated manner to one of the chain links of the second chain, wherein one of the articulated connections between the chain links of the first chain and the spacer component comprises a form-fit hinge, and one of the articulated connections between the chain links of the second chain and the spacer component comprises a form-fit hinge, wherein a distance between the first chain and the second chain decreases from the proximal end to the distal end.

* * * * *